United States Patent [19]

Shen et al.

[11] 4,168,151

[45] Sep. 18, 1979

[54] O-AMIDOPHENYLMORPHOLINE COMPOUNDS

[75] Inventors: Kelvin K. Shen, Fountain Valley, Calif.; Wayne S. Belles, Moscow, Id.

[73] Assignee: United States Borax & Chemical Corporation, Los Angeles, Calif.

[21] Appl. No.: 969,044

[22] Filed: Dec. 13, 1978

Related U.S. Application Data

[62] Division of Ser. No. 930,781, Aug. 3, 1978, Pat. No. 4,153,443, which is a division of Ser. No. 802,606, Jun. 2, 1977, Pat. No. 4,123,251.

[51] Int. Cl.$^2$ .................... A01N 9/22; C07D 295/14
[52] U.S. Cl. ..................................... 71/88; 544/159; 544/166
[58] Field of Search .................... 544/159, 166; 71/88

[56] References Cited

PUBLICATIONS

Meth–Cohn et al, "Chem. Abstracts" vol. 59 (1963), 13965g.

*Primary Examiner*—Alan L. Rotman
*Assistant Examiner*—R. W. Ramsuer
*Attorney, Agent, or Firm*—James R. Thornton

[57] ABSTRACT o-Amidophenylmorpholine compounds having a halo, haloalkyl, lower alkylsulfonyl, halo-lower alkylsulfonyl, or lower alkyl substituent on the aromatic ring para to the morpholino nitrogen. The compounds are useful as herbicides.

12 Claims, No Drawings

O-AMIDOPHENYLMORPHOLINE COMPOUNDS

This is a division of our application Ser. No. 930,781 filed Aug. 3, 1978, now U.S. Pat. No. 4,153,443 (May 8, 1979) which, in turn, is a division of our application Ser. No. 802,606 filed June 2, 1977, now U.S. Pat. No. 4,123,251.

This invention relates to novel o-amidophenylmorpholines including the sulfonilamides.

RELATED APPLICATION

Our copending application, Ser. No. 766,289, filed Feb. 7, 1977, now U.S. Pat. No. 4,133,672, describes and claims a novel class of 4-(2-aminophenyl)morpholine compounds useful as herbicides and intermediates.

BACKGROUND OF THE INVENTION

The synthesis of certain morpholinoaniline compounds is described by Nair and Adams in the *Journal of the American Chemical Society*, Volume 83, pages 3518-3521 (1961). These compounds are prepared by the catalytic or chemical reduction of the corresponding ortho-nitrophenylmorpholine compound according to the following reaction:

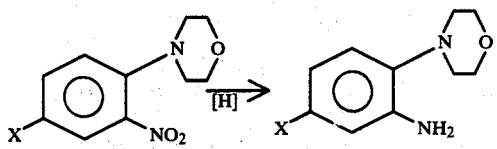

in which X equals hydrogen, chloro, methyl or nitro.

SUMMARY OF THE INVENTION

This invention provides a class of N-(2-amidophenyl)-morpholine compounds of the formula

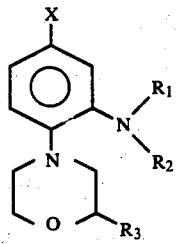

in which x represents lower alkyl, halo, halo-lower alkyl, lower alkylsulfonyl, or halo-lower alkylsulfonyl, $R_1$ represents

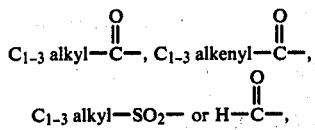

$R_2$ is selected from the group consisting of hydrogen and those groups represented by $R_1$, and $R_3$ is selected from hydrogen and alkyl of 1 to about 3 carbon atoms. The $C_{1-3}$ alkyl and $C_{1-3}$ alkenyl groups may also have substituents such as halo and lower alkoxy, viz., chloro, bromo, fluoro, methoxy. The term "lower alkyl" when used herein is meant to include alkyl groups having up to six carbon atoms. Examples of groups which may be represented by X include chloro, bromo, fluoro, trifluoromethylsulfonyl, trifluoromethyl, methyl, ethyl, propyl, isopropyl, tert-butyl, ethylsulfonyl, cyclopropyl, sec-pentyl, sec-butyl, methylsulfonyl, difluoromethylsulfonyl, isoamyl, and the like. Examples of groups which may be represented by $R_1$ and $R_2$ include acetyl, propionyl, trifluoroacetyl, perfluoropropionyl, cyclopropylcarbonyl, formyl, isobutyroyl, methylsulfonyl, ethylsulfonyl, chloroacetyl, trichloracetyl, acryloyl, methoxylacetyl, chlorodifluoroacetyl, chlorofluoroacetyl, and the like.

The compounds of this invention are useful as herbicides. The preferred compounds for herbicidal activity are those in which $R_2$ and $R_3$ represent hydrogen and X represents a branched chain alkyl group of 3 to about 6 carbon atoms. Especially preferred are the acetanilides in which $R_1$ represents

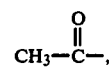

and $R_2$ and $R_3$ represent hydrogen.

The compounds may be prepared by reaction of the corresponding ortho-morpholinoaniline with the corresponding acid anhydride according to the equation:

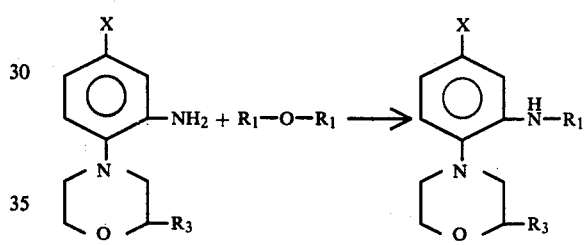

wherein $R_1$, $R_3$ and X have the significance previously assigned.

The reaction takes place using a slight molar excess (about 10–20%) of acetylating agent in the presence of a solvent such as benzene and the glycol ethers at a moderately elevated temperature such as about 50° to 80° C. A tertiary amine catalyst such as pyridine and triethylamine may also be present, but is not essential.

When $R_2$ is a group other than hydrogen, a large excess of the acetylating agent is employed without a solvent. Reaction temperatures in excess of 100° C. are also employed so as to push the reaction close to completion.

Generally, the desired product can be isolated by pouring the reaction product mixture into ice water and separated by filtration of the crystalline precipitate or extraction with a water-immiscible solvent from which the product can be isolated. The products are usually crystalline solids which can be purified by recrystallization such as from hexane.

When $R_1$ is

and $R_2$ is hydrogen, the compound may be prepared by reaction of the morpholinoaniline with an excess of formic acid at elevated temperatures to produce the formamido derivative.

As an alternative to the acid anhydrides, the acid halides such as the acyl chlorides and bromides as well as the corresponding sulfonyl halides may be employed as reactants.

The following examples illustrate the preparation of representative compounds of the invention.

EXAMPLE I 4-(2-Acetamido-4-trifluoromethylphenyl)morpholine

A mixture of 40 g. (16 mmoles) of 4-(2-amino-4-trifluoromethylphenyl)morpholine and 2.2 g. (22 mmoles) of acetic anhydride in 40 ml. of dry dimethoxyethane was heated at 70° C. for 10 hours. The reaction mixture was cooled to room temperature and then the solvent removed by evaporation under reduced pressure. The residue was dissolved in 100 ml. of methylene chloride and the solution washed with 5% sodium bicarbonate solution. After drying over anhydrous sodium sulfate, the solution was filtered and evaporated under reduced pressure. The residue was dissolved in n-hexane from which it crystallized to give 4.4 g. (96%) of the desired product melting at 85° C.

EXAMPLE II 4-(2-acetamido-4-ethylphenyl)morpholine

A mixture of 5.7 g. (27 mmoles) of 4-(2-amino-4-ethylphenyl)morpholine and 3.1 g. (30 mmoles) of acetic anhydride in 70 ml. of dry dimethoxyethane was heated at 60° C. for 5 hours. The resultant mixture was poured into an excess of ice-water, precipitating the product. Filtration gave 6.0 g. (90%) of 4-(2-acetamido-4-ethylphenyl)morpholine, m.p. 82° C.

EXAMPLE III 4-(2-trifluoroacetamido-4-tert-butylphenyl)morpholine

A mixture of 5.0 g. (21 mmoles) of 4-(2-amino-4-tert-butylphenyl)morpholine, 10.0 g. (48 mmoles) of trifluoroacetic anhydride and 2 drops of pyridine in 40 ml. of benzene was heated at 60° C. for one hour and then allowed to stand at room temperature overnight. The mixture was then poured into an excess of ice-water, neutralized with sodium carbonate and the organic phase separated. The benzene solution was dried over anhydrous sodium sulfate, filtered and the solvent removed by evaporation under reduced pressure to give the desired product as a dark red solid (5.1 g.; 74%) melting at 89°-90° C.

EXAMPLE IV 4-(2-acetamido-4-tert-butylphenyl)morpholine

A mixture of 12.5 g. (53 mmoles) of 4-(2-amino-4-tert-butylphenyl)morpholine and 8.7 g. (85 mmoles) of acetic anhydride in 40 ml. of dimethoxyethane was heated at 70° C. for 15 hours. The cooled reaction mixture was then poured into an excess of ice-water and the water mixture extracted twice with 70 ml. of methylene chloride. The combined extracts were dried over anhydrous sodium slfate, filtered and evaporated under reduced pressure. The residue was recrystallized from a 10:1 mixture of n-hexane and chloroform to give 12.5 g. (85%) of the desired product, m.p. 112°-113° C.

EXAMPLE V 4-(4-tert-butyl-2-diacetylaminophenyl)morpholine

A mixture of 2.0 grams (9 mmoles) of 4-(2-amino-4-tert-butylphenyl)morpholine and 4.0 g. of acetic anhydride was heated at 130° C. for 14 hours. The resultant mixture was poured into an excess of ice-water. The water mixture was extracted with methylene chloride, the extract washed with 5% sodium bicarbonate solution and dried over anhydrous sodium sulfate. The solvent was evaporated under reduced pressure and the residue then passed through a 3×70 cm. silica gel column with methylene chloride as eluant. The first major fraction gave the product which crystallized upon addition of n-hexane. There was obtained 0.3 g. of product melting at 128° C.

EXAMPLE VI 4-(2-trifluoromethanesulfamido-4-tert-butylphenyl)morpholine

To a stirred solution of 1.1 g. (5 mmoles) of 4-(2-amino-4-tert-butylphenyl)morpholine in 30 ml. of dry methylene chloride was added drop-wise 1.4 g. (5 mmoles) of trifluoromethanesulfonic anhydride and then 0.5 g. (5 mmoles) of triethylamine at about 5° C. The resultant dark purple mixture was filtered and the solvent removed by evaporation under reduced pressure. The residue was recrystallized from a 1:5 mixture of n-hexane-chloroform to give 1.3 g. (76%) of the desired product, m.p. 121°-122.5° C.

EXAMPLES VII–XXX

The following are examples of the many other compounds of this invention which may be prepared by the procedures described above.

VII. 4-(2-acetamido-4-trifluoromethylsulfonylphenyl)morpholine, m.p. 123°-126° C.

VIII. 4-(2-acetamido-4-chlorophenyl)morpholine, m.p. 109°-112° C.

IX. 4-(2-acetamido-4-methylphenyl)morpholine, m.p. 119°-119.5° C.

X. 4-(2-acetamido-4-tert-amylphenyl)morpholine, m.p. 69° -72° C.

XI. 4-(2-chlorodifluoroacetamido-4-tert-butylphenyl)morpholine, m.p. 89°-90° C.

XII. 4-(2-formamido-4-tert-butylphenyl)morpholine, m.p. 183°-185° C.

XIII. 4-(2-chloroacetamido-4-tert-butylphenyl)morpholine, m.p. 84° C.

XIV. 4-(2-propionamido-4-tert-butylphenyl)morpholine, m.p. 67° C.

XV. 4-(2-isobutyroamido-4-tert-butylphenyl)morpholine, m.p. 94°-95° C.

XVI. 4-(2-cyclopropylcarbonylamino-4-tert-butylphenyl)morpholine, m.p. 124° C.

XVII. 4-(2-methanesulfonylamino-4-tert-butylphenyl)morpholine, m.p. 189°-190° C.

XVIII. 4-(2-acetamido-4-isopropylphenyl)morpholine, m.p. 110° C.

XIX. 4-[2-(β-chloropropionamido)-4-tert-butylphenyl]morpholine, m.p. 107° C.

XX. 4-(2-trichloroacetamido-4-tert-butylphenyl)morpholine, m.p. 118.5°-122° C.

XXI. 4-(2-acryloamido-4-tert-butylphenyl)morpholine, semi-solid

XXII. 4-[2-(N-acetyl-N-trifluoromethanesulfonyl)amino-4-tert-butylphenyl]morpholine, oil XXIII. 4-(2-methoxyacetamido-4-tert-butylphenyl)morpholine, m.p. 94.5°-95.5° C.

XXIV. 4-(2-acetamido-4-methylsulfonylphenyl)morpholine, m.p. 155° C.

XXV. 4-(2-methoxyacetamido-4-tert-amylphenyl)morpholine

XXVI. 2-methyl-4-(2-acetamido-4-isopropylphenyl)morpholine, oil

XXVII. 4-(2-acetamido-4-cyclopropylphenyl)morpholine

XXVIII. 4-(2-acetamido-4-sec-butylphenyl)morpholine

XXIX. 4-(2-acetamido-4-difluoromethylsulfonylphenyl)morpholine

XXX. 4-(2-perfluoropropionamido-4-tert-butylphenyl)morpholine

The compounds of this invention are useful as herbicides. They can be applied as either a pre-emergence or a post-emergence treatment; that is, they can be applied to soil in which the weeds will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds may be applied to the soil surface prior to emergence of the weeds or, preferably, are incorporated, such as by mixing into the top 1 to 3 inches of the soil prior to planting the crop. When used as a post-emergence treatment, it is preferred that a directed spray be employed, thereby directing the application of the herbicide unto the foliage of the weeds and away from the foliage of the desirable crop plants. Weeds, as used herein, is meant to include any plant growth which is undesirable.

The compounds are especially useful for selectively controlling weeds in the presence of desirable crops such as peanuts, corn, and cotton. The weeds controlled include many of the broadleaf weeds such as lambsquarter, mustard, pigweed, velvetleaf, cocklebur, and jimson weed.

Generally, an application rate of from about 0.5 to about 15 pounds of one or more of the active compounds per acre is effective in controlling weed growth. Preferably, an application rate in the range of about 0.75 to 5 pounds per acre is employed.

The following examples illustrate the herbicidal activity of representative compounds of this invention.

EXAMPLE XXXI

The compounds to be tested were evaluated as both a pre-emergence and post-emergence treatment. Greenhouse flats were planted to soybeans (SB), velvetleaf (VL), oats (O) and millet (M). The flats were sprayed on the same day as planting with an ethanol solution (sometimes containing added dioxane) of the compound to be tested at a rate of 5 pounds per acre. Another set of flats with the same plants was treated after the plants had emerged and were about one inch in height. These flats were also sprayed with the solution of the compound to be tested at a rate of 5 pounds per acre. The flats were kept in the greenhouse and watered when needed. Twenty-one days after treatment, the flats were examined and the plants rated for herbicidal activity on a 0-9 scale in which 0=no effect, 5=substantial injury with some kill and 9=complete kill. Results are shown in Table I. 4-(2-Amino-4-methylphenyl)morpholine, a known compound, is included for comparison.

TABLE I

| Compound (Ex.) | ACTIVITY | | | | | | | |
|---|---|---|---|---|---|---|---|---|
| | Pre | | | | Post | | | |
| | SB | VL | O | M | SB | VL | O | M |
| I | 2 | 7 | 1 | 5 | 2 | 9 | 1 | 7 |
| II | 2 | 9 | 3 | 9 | 3 | 9 | 5 | 9 |
| III | 0 | 9 | 1 | 8 | 9 | 9 | 5 | 9 |
| IV | 9 | 9 | 9 | 9 | 9 | 9 | 9 | 5 |
| V | 3 | 9 | 7 | 1 | 3 | 8 | 1 | 5 |
| VI | 0 | 9 | 0 | 1 | 1 | 9 | 0 | 5 |
| VII | 0 | 0 | 0 | 0 | 1 | 8 | 0 | 0 |
| VIII | 0 | 9 | 1 | 1 | 0 | 8 | 0 | 0 |
| IX | 1 | 8 | 1 | 0 | 2 | 8 | 0 | 0 |
| X | 0 | 5 | 0 | 0 | 3 | 9 | 0 | 0 |
| XI | 0 | 9 | 1 | 5 | 4 | 9 | 5 | 8 |
| XII | 6 | 9 | 2 | 1 | 7 | 9 | 3 | 6 |
| XIII | 0 | 0 | 0 | 0 | 1 | 6 | 0 | 0 |
| XIV | 2 | 7 | 2 | 2 | 6 | 9 | 3 | 8 |
| XV | 2 | 9 | 0 | 8 | 6 | 8 | 1 | 1 |
| XVI | 1 | 8 | 2 | 5 | 3 | 8 | 0 | 0 |
| XVII | 0 | 9 | 0 | 2 | 2 | 2 | 0 | 0 |
| XVIII | 4 | 9 | 6 | 9 | 9 | 9 | 9 | 9 |
| XIX | 0 | 0 | 0 | 0 | 1 | 8 | 1 | 1 |
| XX | 0 | 0 | 0 | 0 | 1 | 9 | 0 | 0 |
| XXI | 0 | 9 | 0 | 0 | 3 | 9 | 1 | 2 |
| XXII | 0 | 5 | 0 | 1 | 0 | 9 | 0 | 0 |
| XXIII | 2 | 9 | 0 | 5 | 9 | 9 | 1 | 9 |
| 4-(2-Amino-4-methyl phenyl)morpholine | 0 | 0 | 0 | 0 | 0 | 2 | 0 | 0 |

EXAMPLE XXXII

Compound IV was evaluated as pre-emergence herbicide in greenhouse tests with a broad group of crops and weeds at 1 pound per acre. An ethanol solution of the compound was sprayed on the soil and mixed into the top 1 inch thereof. Immediately thereafter, crops and weeds were planted in the treated soil. The flats were kept in the greenhouse and watered as needed. Twenty-one days after treatment, the plants were rated on a 0 to 9 scale. Where two numbers are used, i.e. 8/4, the first number represents the percent kill and the second number is the injury to the remaining plants, using the following scale.

0 = no effect
1 = <10% injury
2 = 10–40% injury
3 = 40–70% injury
4 = >70% injury
5 = <25% kill
6 = 25–50% kill
7 = 50–75% kill
8 = 75–99% kill
9 = 100% kill The results are given in Table II and are an average of two replicates.

TABLE II

| Plants | HERBICIDE ACTIVITY |
|---|---|
| Corn | 0/2 |
| Cotton | 0 |
| Dry beans | 0/1 |
| Peanuts | 0 |
| Rice | 5/3 |
| Soybeans | 0/1 |
| Wheat | 0/1 |
| Alfalfa | 9 |
| Cocklebur | 9 |
| Jimsonweed | 9 |
| Lambsquarters | 9 |
| Morningglory | 0/1 |
| Mustard | 9 |
| Prickly sida | 5/2 |
| Pigweed | 9 |

TABLE II-continued

| Plants | HERBICIDE ACTIVITY |
| --- | --- |
| Sesbania | 0/1 |
| Velvetleaf | 9 |
| Barnyard grass | 8/3 |
| Foxtail | 0/4 |
| Johnsongrass | 0/2 |
| Wild oats | 8/3 |

Since a relatively small amount of one or more of the active compounds should be uniformly distributed over the area to be treated, they preferably are formulated with conventional herbicide carriers, either liquid or solid. Thus, the compounds can be impregnated on or admixed with a pulverulent solid carrier such as lime, talc, clay, Bentonite, calcium chloride, vermiculite and the like. Alternatively, they can be dissolved or suspended in a liquid carrier such as water, kerosene, alcohols, diesel oil, mineral oil, xylene, benzene, glycols, ketones, and the like.

A surfactant is preferably included to aid in dispersion, emulsification and coverage. The surfactant can be ionic or non-ionic and may be liquid or solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium slats of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

Various changes and modifications of the invention can be made, and, to the extent that such variations incorporate the spirit of this invention, they are intended to be included within the scope of the appended claims.

What is claimed is:

1. A compound of the formula

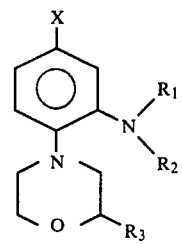

wherein X is selected from lower alkyl, halo, halo-lower alkyl, lower alkylsulfonyl, and halo-lower alkylsulfonyl, $R_1$ is

$R_2$ is hydrogen, and $R_3$ is selected from hydrogen and alkyl of 1 to 3 carbon atoms.

2. A compound according to claim 1 in which X is a branched chain alkyl of 3 to about 6 carbon atoms.

3. A compound according to claim 1 in which X is tert-butyl.

4. The compound according to claim 1, 4-(2-formamido-4-tert-butylphenyl)morpholine.

5. A herbicidal composition comprising an herbicidally effective amount of a compound according to claim 1, a surfactant and an inert carrier therefor.

6. The method of controlling undesirable plant growth which comprises applying a phytotoxic amount of a compound according to claim 1 to the locus of said plants.

7. The method according to claim 6 in which said compound is applied pre-emergence to the soil.

8. The method according to claim 6 in which said compound is applied at a rate of about 0.75 to 5 pounds per acre.

9. The method according to claim 6 in which X is a branched chain alkyl of 3 to about 6 carbon atoms.

10. The method according to claim 6 in which said compound is 4-(2-formamido-4-tert-butylphenyl)morpholine.

11. The method according to claim 6 in which said X is tert-butyl.

12. The method according to claim 7 in which said compound is mixed into the top 1–3 inches of soil prior to planting crop seeds.

* * * * *